United States Patent [19]

North, Jr.

[11] 4,074,562

[45] Feb. 21, 1978

[54] METHOD AND APPARATUS FOR MEASURING FLUID SPECIFIC GRAVITY

[75] Inventor: Howard L. North, Jr., Newfoundland, N.J.

[73] Assignee: Becton, Dickinson and Company, East Rutherford, N.J.

[21] Appl. No.: 759,011

[22] Filed: Jan. 13, 1977

[51] Int. Cl.² .............................................. G01N 9/00
[52] U.S. Cl. .................................................... 73/32 A
[58] Field of Search ............................. 73/32 A, 32 R

[56] References Cited

U.S. PATENT DOCUMENTS

| | | | |
|---|---|---|---|
| 2,956,431 | 10/1960 | Westerheim | 73/32 A |
| 3,420,092 | 1/1969 | Dorsch | 73/32 A |
| 3,444,723 | 5/1969 | Wakefield | 73/32 A |
| 3,516,283 | 6/1970 | Abbotts | 73/32 A X |
| 3,523,446 | 8/1970 | Kratky et al. | 73/32 A |
| 3,729,982 | 9/1971 | Senda | 73/32 A |
| 3,831,433 | 8/1974 | Kovacs et al. | 73/32 A |

*Primary Examiner*—James J. Gill

*Attorney, Agent, or Firm*—Kane, Dalsimer, Kane, Sullivan & Kurucz

[57] ABSTRACT

A method and apparatus for measuring specific gravity of fluids such as urine. The apparatus includes a housing and a hollow tube mounted in the housing and open at both ends. The housing is adapted for communication with a source of fluid to be introduced into one end of the hollow tube. The housing is also adapted for connection of pressure differential structure to the other end of the hollow tube for causing fluid to flow from the fluid source through the hollow tube. The tube is vibrated with the fluid therein and electronic response means are employed to measure the vibration frequency of the tube and sample therein and compare the measurement with a predetermined reference frequency to determine the specific gravity of the fluid. The forces to vibrate the tube are produced electromagnetically by impressing an alternating current on the tube itself which is located within the field of a magnet. The alternating currents are produced by making the tube a short circuited single turn secondary of a transformer, the primary of which is connected to a source of alternating voltage and current.

19 Claims, 7 Drawing Figures

METHOD AND APPARATUS FOR MEASURING FLUID SPECIFIC GRAVITY

BACKGROUND OF THE INVENTION

In various environments and different types of technical fields, it often becomes necessary to measure the specific gravity of a fluid. In such circumstances, it is desirable to have a convenient, fast, accurate determination of the specific gravity which is not subject to operator error or operator induced variation. This is particularly true in the medical profession where body fluids as urine are being analyzed. Urine specific gravity is one criteria in some diagnostic techniques.

Naturally in the medical profession it is of utmost importance to be as accurate, as fast and as convenient as possible in the testing procedures.

Furthermore, when dealing with a fluid such as urine there are other parameters which must be given consideration. Specimen temperature can affect the test results especially when body temperature urine is being assayed. Naturally in dealing with body fluids the problem of cross contamination also must be contended with. Also, it is of advantage to be able to handle small volumes and to accurately test the sample volumes to produce an accurate specific gravity determination. It should also be kept in mind that the testing equipment should be as mobile, portable and compact as possible while being of low cost manufacture and easy and inexpensive to utilize. It is another advantage to be able to obtain dependable use over as long a period of time as possible.

SUMMARY OF THE INVENTION

With the above criteria in mind, it is among the primary objectives of the present invention to provide a method and apparatus for convenient, fast, accurate determination of specific gravity of a fluid such as urine. The structure and procedure is designed so that operator error and operator induced variation is eliminated. Furthermore, the system is designed to provide readings of specific gravity which are automatically compensated for the effect of specimen temperature. A fast accurate readout can be automatically obtained with a small sample volume and additionally there is no danger of cross contamination.

It is also among the primary objectives of the present invention to provide a vibrating tube density measuring device with the means to vibrate the tube being comprised of a transformer of which the tube itself is a single turn short circuited secondary. The resultant current and magnetic field reacts with the field of a permanent magnet to produce excitation forces on the tube to drive it to resonance when the transformer primary is connected to suitable electronic amplifier means.

A further objective is to provide a signal processing system wherein the signal is processed by heterodying the sample frequency with a reference frequency to produce a digital readout of specific gravity over a limited range such as 1.0 - 1.1. The heterodyne feature allows direct digital readout without the use of analog-to-digital converters. This simplifies the circuitry and provides accuracy at low cost.

Furthermore, another object is to compensate for temperature conditions by use of a thermistor sensor varying the frequency of the reference oscillator to provide an accurate measuring system.

In summary, the method and apparatus for measuring the fluid specific gravity includes a housing and a hollow tube mounted in the housing. The tube is open at both ends. Means is on the housing for communication with a source of fluid to be introduced into one end of the hollow tube. Means is on the housing for connection of pressure differential means to the other end of the hollow tube for causing fluid to flow from the liquid source through the hollow tube. Vibration means is provided for vibrating the tube with fluid therein. Finally, response means is provided to measure the vibration frequency of the tube and sample therein and compare the measurement with a predetermined reference frequency to determine the specific gravity of the fluid.

With the above objectives among others in mind, reference is made to the attached drawings.

DESCRIPTION OF THE PREFERRED EMBODIMENTS

The drawings show the apparatus of the invention as utilized in an instrument for determining urine specific gravity. Naturally other fluids can be utilized with the apparatus in determining their specific gravities as well.

Figure 1:
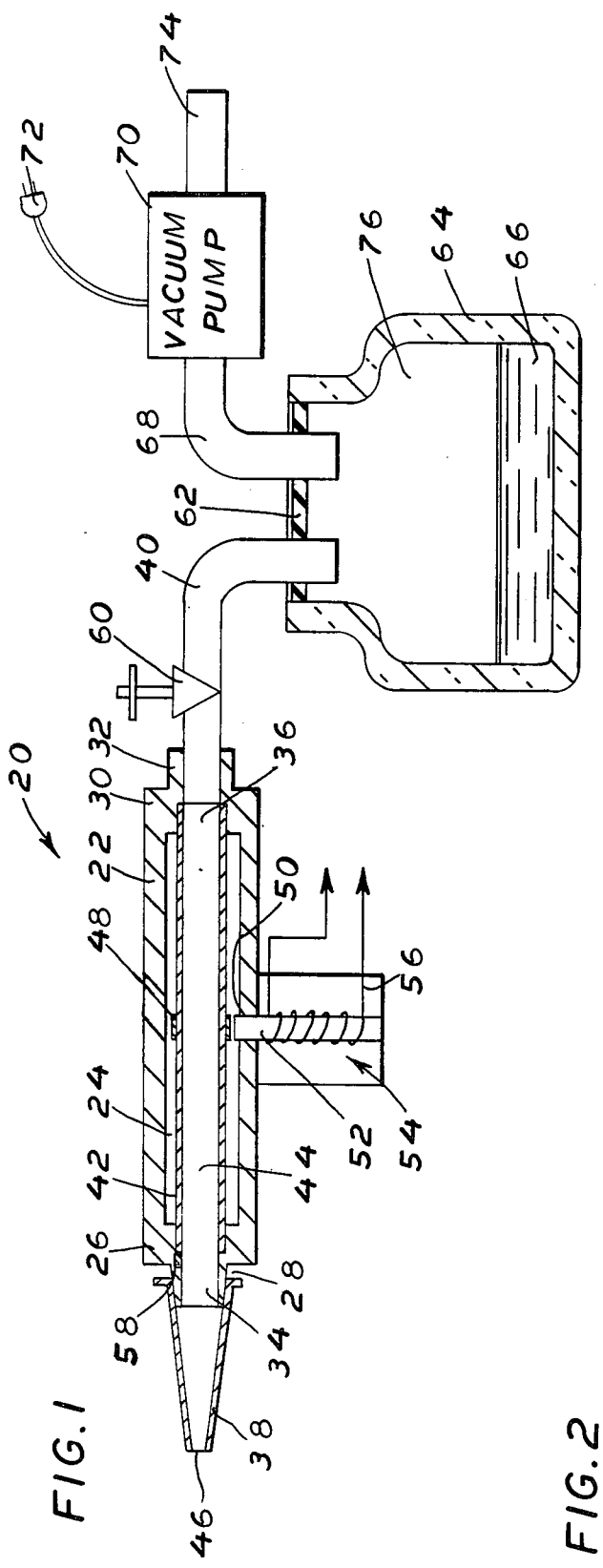
FIG. 1 is a schematic sectional view of the apparatus of the invention.

FIG. 1 shows the device 20 in schematic form which includes an outer housing 22 of substantially tubular configuration with a hollow interior chamber 24 therein. One end wall 26 of the housing terminates in a projection 28 and the other end wall 30 of the housing terminates in a projection 32. A passageway 34 extends through projection 28 and end wall 26 into communication with interior chamber 24 and similarly a passageway 36 extends through end wall 30 and projection 32 into communication with chamber 24. Thus a continuation passageway extends from end to end of the housing 22.

Mounted on projection 28 is a conically shaped disposable tip 38 which can be manufactured of a plastic or similar low cost material for disposability after use. The tip 38 is frictionally engaged with projection 28 so that it can be easily attached and removed from the housing. The housing is constructed of a rigid material and has a tube 40 extending from passageway 36. The tube 40 is mounted in passageway 36 in a conventional fashion such as by an epoxy or by frictional interengagement. The tube is preferably flexible; however, if desired it can be semi-rigid or rigid.

Mounted within chamber 24 in housing 22 is an elongated glass tube 42. One end of the glass tube is mounted by a glass to metal bond or by any suitable means to a recess in end wall 26 and the other end of the tube 42 is similarly mounted in the end wall 30. The passageway 44 through tube 42 communicates with passageways 34 and 36 and thus provides a continuous passage from the forward open end 46 of tip 38 into tube 40 extending from the opposite end of the housing 22.

Intermediate the ends of tube 42 and surrounding the outer surface thereof is a band 48 of magnetic material which is also positioned in a conventional fashion such as by friction on the outer surface of tube 42. Aligned with band 48 is a side opening 50 in the wall of housing 22 through which extends the bar 52 of an electromagnet 54. The coil 56 of the electromagnet is connected to driving circuitry suitable for operating the device. The power source for the electromagnet is not shown; however, it is of a conventional and well known type.

Mounted in the wall 26 of housing 22 close to projection 28 is a thermistor temperature sensor 58 which is interconnected with the remaining electronics of the system in a conventional fashion so as to monitor the temperature at the inlet to the housing and particularly of the fluid passing into tube 42.

Intermediate the ends of tube 40 extending from one end of the housing is a valve 60 which provides a means for starting and stopping fluid flow through tube 42. Tube 40 extends through the cover 62 of a waste reservoir 64. The waste 66 which has been tested by passage through tube 42 is collected in reservoir 64. The top 62 of the reservoir forms a seal for the container with tube 40 passing through one opening therein and a tube 68 passing through a second opening therein which is connected to a vacuum pump 70. The vacuum pump is of a conventional type which can be plugged into a normal 110 line voltage outlet by means of plug 72. The vacuum pump has a vent 74 for removal of air as it operates on the system. Thus, when the vacuum pump is plugged in and started and valve 60 is opened the vacuum pump will create a vacuum within the interior chamber 76 of reservoir 64 which in turn will draw fluid into the end 46 of tip 38 and through tube 42, then out through tube 40 into the reservoir 64.

Thus, in operation, when tip 46 is inserted into a urine specimen container and the vacuum pump 70 is started and valve 60 is opened, the urine sample is aspirated into device 20 through plastic tip 38, through the glass tube 42 and into the waste reservoir 64 under the pressure differential created by the vacuum pump 70. It is contemplated that a syringe type pump with appropriate valves could be used to aspirate a sample into tube 42 in place of the vacuum pump depicted. The tube 42 and sample of urine contained therein are vibrated by the driving electromagnet 54 acting on the band of magnetic material 48 affixed to glass tube 42. The vibration is produced at the natural frequency of the glass tube/sample by suitable electronic circuitry. Thermistor 58 senses the housing temperature which is close to the sample temperature. Alternatively, the thermistor 58 could be immersed in the sample passing through projector 28.

Alternatively, the fluid specific gravity may be measured by a fluid which is stationary in the tube in contrast to passing through the tube as described above. With a stationary fluid sample in the tube, the measurement is made after a few seconds of time to allow for thermal stabilization and vibration stabilization. Otherwise, the sequence of signal processing is identical with the embodiments where the fluid is passing through the tube.

Figure 2:
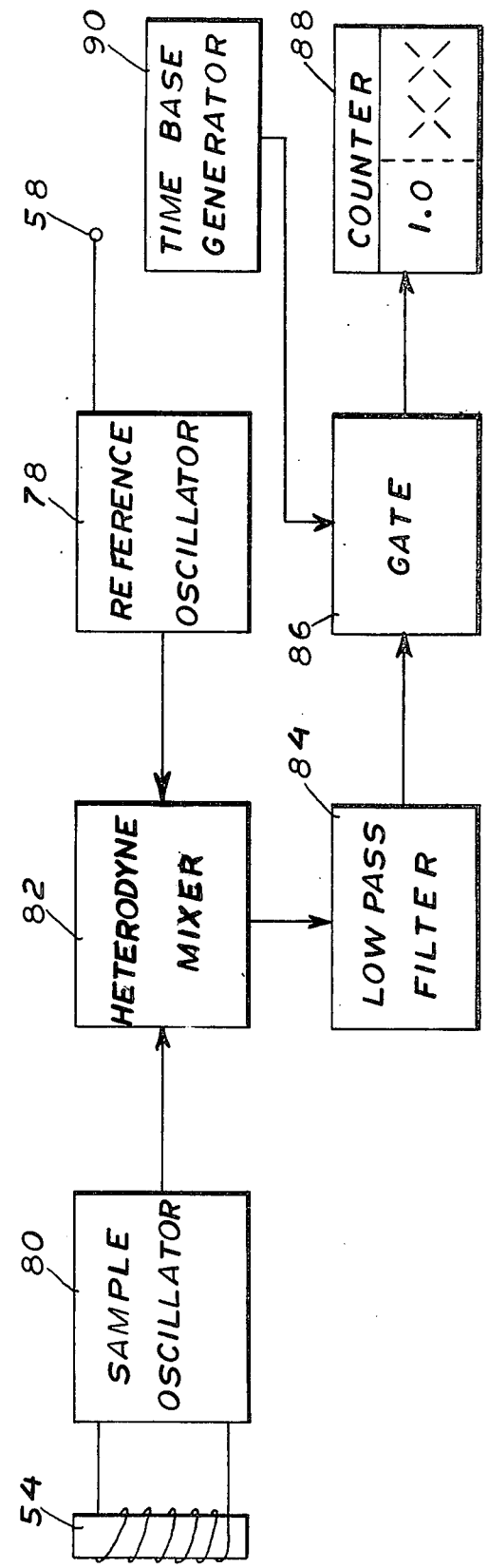
FIG. 2 is a block diagram of the electronic portion of the apparatus of the invention for processing the signal frequency.

The general sequence of signal processing is depicted in FIG. 2 where the thermistor 58 biases a reference oscillator 78 and the electromagnet 54 is connected to a sample oscillator 80. Thereafter, the signals from the reference oscillator and the sample oscillator are passed to and heterodyned by mixer 82 the output of which consists of these two signals and their sum and difference. The output from the heterodyne mixer is directed through a low pass filter 84 to eliminate the two original signals and their sum to produce the difference between the two signals and thence through a gate 86 to a counter 88 where the specific gravity result is displayed. A time base generator 90 controls the gate to establish the time duration for the operation of counter 88 and to provide means for calibration adjustment.

The sample oscillator 80 frequency is dependent on the density of the fluid in the tube, the tube density, and the tube stiffness. As the fluid density increases, the sample frequency will decrease. For a very small density range, for example, 1.0 to 1.1 gm/cm$^3$ the relation is very close to linear. The reference oscillator 78 is set so the reference frequency equals the sample frequency when the fluid density equals 1.00 gm/cm$^3$. The two signals are heterodyned and the difference in frequency between the reference frequency and the sample frequency is applied as an input to the counter 88. The time base of the counter and sample frequency selected so that the count corresponds numerically to the last two digits of specific gravity denoted as XX in 1.0 XX in FIGS. 2 and 3.

By filling the tube 42 with distilled water and adjusting the reference frequency, the display is set to 0 (1.000). By filling tube 42 with a standard solution of known specific gravity say 1.090, and adjusting the time base generator 90, the display is set to the correct value, that is 1.090 with the product of the difference between the reference frequency and the sample frequency multiplied by the time base being 90. The thermistor 58 biases reference oscillator 78 so that the display always reads 1.000 as the sample and ambient temperature changes when using distilled water and compensates for fluid density changes with temperature and vibrating tube elasticity changes with temperature.

Figure 3:
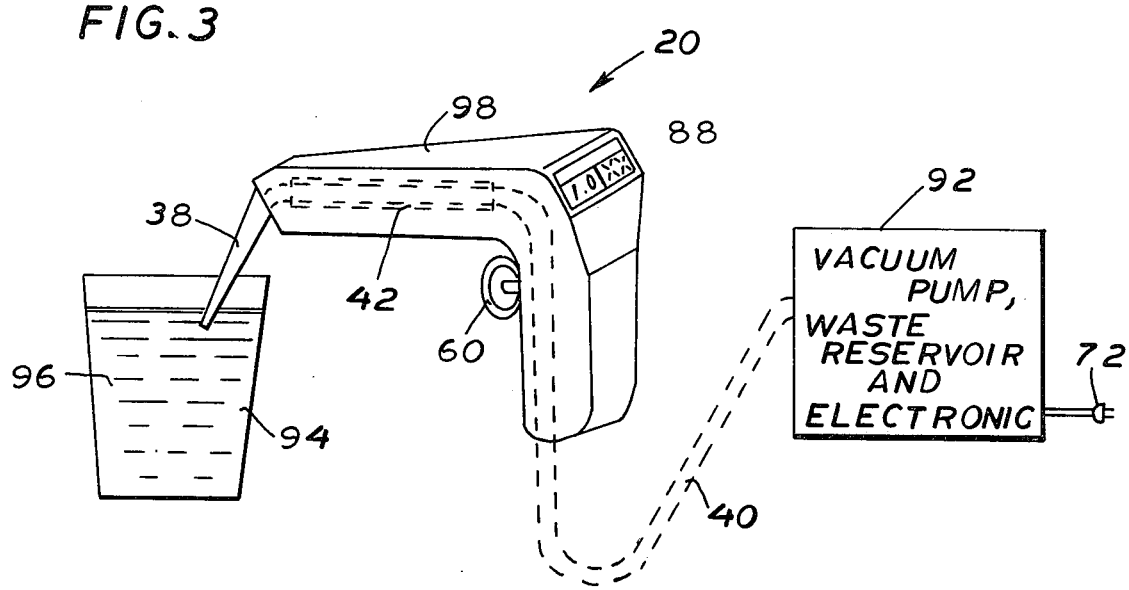
FIG. 3 is a perspective view of the apparatus of the invention shown in position to receive a sample of fluid.

Device 20 may be packaged as a pistol-like instrument as depicted in FIG. 3 with a remote water reservoir, vacuum pump, and electronics contained separately within housing 92 or the entire system may be packaged in one hand-held unit operated by internal battery power.

As shown in FIG. 3, a container 94 containing a urine specimen 96 is positioned to have disposable tip 38 inserted therein. Valve 60 forms a trigger for aspirating the specimen and may be manually controlled or operated by a suitable timing device or may actuate a switch to operate the vacuum pump for a suitable time period. The urine passes through tip 38, through vibrating tube 42 and through flexible tube 40 into the separately contained waste reservoir. Some electronics are housed in the pistol-like unit such as a thermistor, and the driving electromagnet along with the read-out display. Valve 60 is a push button type which operates the system and also can be connected to operate the display. It is contemplated that by a conventional means the valve can be also utilized to eject the disposable plastic tip 38 after the urine sample has been processed and the specific gravity determined. However, naturally the tip 38 can also be removed by other means such as by mere manual disengagement. It is also contemplated that the top surface 98 of the pistol housing can be open or transparent so that the tube vibrating within the housing can be observed to insure that the tube is full of liquid and free of air bubbles.

Tube 42 can be made from a glass material as described above or can be constructed of a thinner wall stainless steel. By use of glass, one can observe the inside of tube 42 to monitor the flow, and particularly to ensure that no bubbles are present in the specimen. On the other hand, it is possible to get much thinner walls with stainless tubing and the steel could be welded or brazed into the housing ends for support. Additionally, the stainless steel, being magnetic and electronically conductive, could be driven directly without the necessity of the addition of metal ring 48 applied to tube 42.

Processing of the signal as depicted in FIG. 2 gives an approximation to exact density when calibrated at two points such as specific gravity readings of 1.000 and 1.060. The mathematical expression for density difference is given by the following equation (exactly)

$$:\Delta d = (d_1 - d_2) = K(\frac{1}{f_1^2} - \frac{1}{f_2^2})$$

It can thus be seen that we are dealing with an inverse square law function which we have approximated with a straight line over a limited range. For a vibrating tube with a mass of metal per unit length equal to that of the sample per unit length and calibrated at specific gravities of 1.000 and 1.060 the maximum error is 0.033% at a specific gravity of 1.030. In the event that it is desired to improve accuracy or to accommodate a larger range in specific gravities it is possible to use one of the optional schemes depicted in FIGS. 4 and 5 for processing the signal frequency.

Figure 4:
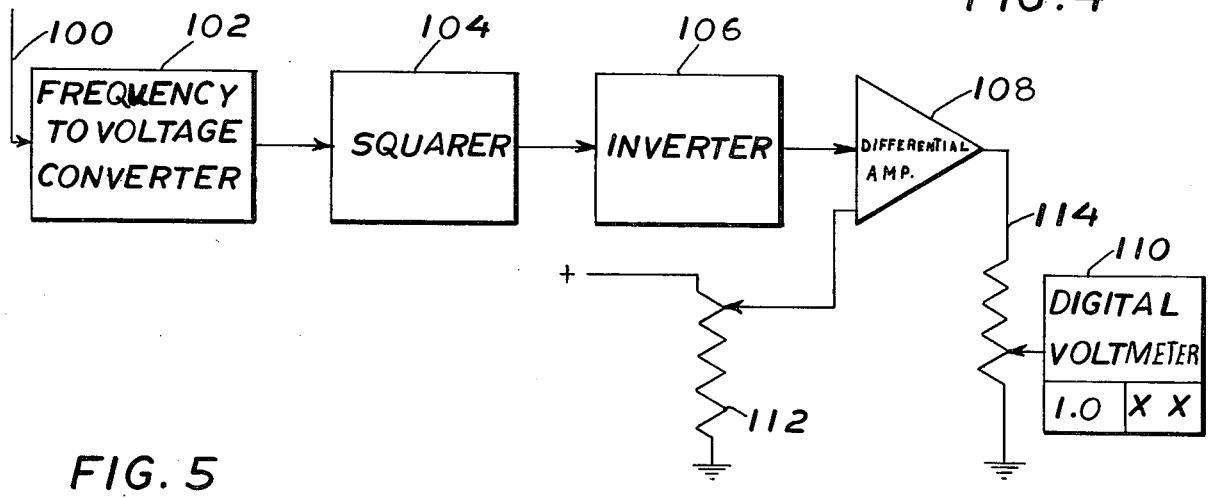
FIG. 4 is a schematic block diagram of an alternative electronic arrangement for processing the signal frequency.

In FIG. 4 the signal 100 from the vibrating tube 42 is passed to a frequency to voltage converter 102 and is then processed sequentially through a squarer 104, an invertor 106, a differential amplifier 108, and a digital voltmeter 110 for display purposes. Naturally conventional zero adjustment means 112 is provided in communication with the differential amplifier 108. Similarly, a calibration adjustment means 114 is provided in communication with the digital voltmeter 110.

Figure 5:
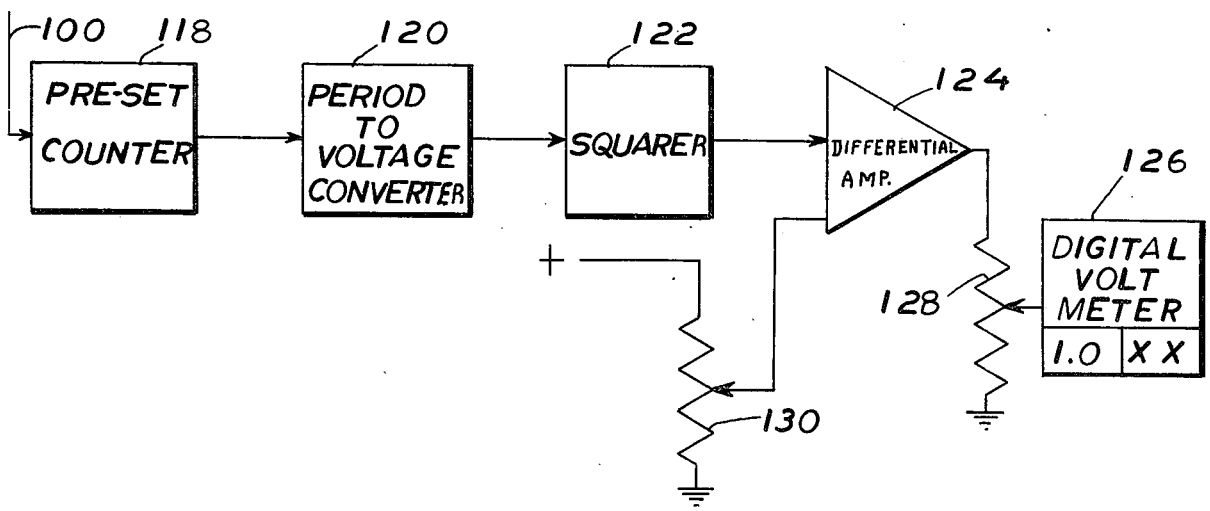
FIG. 5 is a second alternative block diagram for processing the signal frequency.

In the option of FIG. 5 the sample frequency 100 from tube 42 is fed to a preset counter 118 to develop a time period which is inversely proportional to the sample frequency. This time period is applied to a time period to voltage converter 120 to produce a voltage which is inversely proportional to the sample frequency. The signal then passes to a squarer 122 to produce a voltage which is inversely proportional to the square of the sample frequency and then into a differential amplifier 124 and finally to the digital voltmeter 126 for display. Once again calibration adjustment means 128 is provided for the digital voltmeter and a zero adjustment means 130 is provided for the differential amplifier.

No detailed schematic circuits are shown since the above described functional elements are readily implemented by various known electronic systems and designs utilized conventionally in the art.

Figure 6:
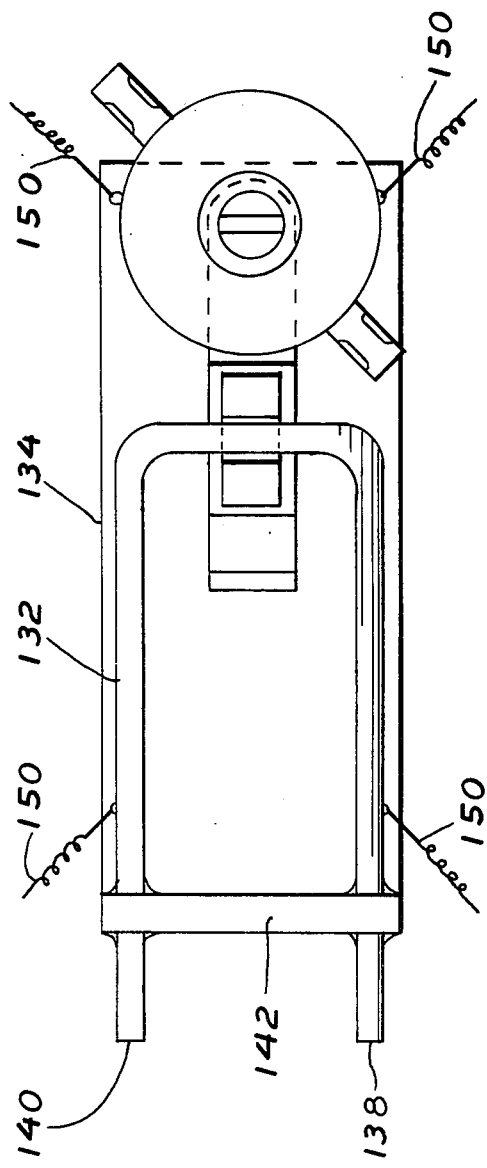
FIG. 6 is a top plan view of an alternative apparatus.
Figure 7:
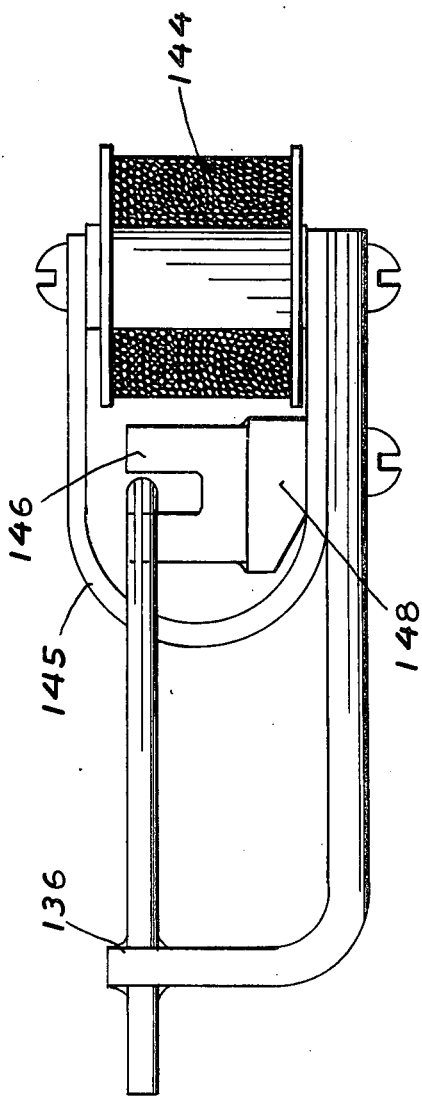
FIG. 7 is a side elevation view thereof.

An alternative structure is depicted in FIGS. 6 and 7 with the primary difference being in the configuration of the hollow tube in the housing of the device. A U-shaped tube 132 is mounted in the housing 134 by conventional means such as silver brazing 136 with one open end 138 of the tube exposed for introduction of the sample and the other open end 140 positioned outside of the housing for exit of the sample. An appropriate disposable tip can be attached to the sample entrance end 138 and the tube 40 to the waste reservoir can be attached to the sample exit end 140. An upstanding support bar 142 holds the U-shaped tube 132 in an elevated position. An electromagnet 144 is mounted on the housing and is magnetically coupled to the tube 132 via structure 145. A permanent magnet 146 of U-shape configuration is positioned so that the tube can pass between legs thereof. The magnet is mounted on support 148. The electromagnet 144 is suitably electrically connected to cause vibration of the tube 132 with the fluid therein.

By supporting the sample tube adjacent the ends of its legs, the closed end forms a cantilever-like beam which is unsupported at one end and which will change its natural frequency due to the change in mass (specific gravity) of the fluid inside the tube. The cantilever form of support also avoids the phenomenon of changing temperatures causing changing tension, stiffness, and resonant frequency of the tube (like a violin string).

The assembly is very small and compact. It can easily be fitted into a hand-held instrument such as housing 20. If further reduction in size is desired, the electromagnet 144 could be placed inside the U-tube. It should be noted in all of these devices that the manufacturing and use costs are very low.

The assembly of FIGS. 6 and 7 is supported on tension springs 150 to reduce the effect of variations in support of the instrument housing. As discussed above, a thin stainless steel tube has been found to operate effectively and stainless steel can be used in this embodiment for the support as well as the tube. This type of material provides some compensation for the effects of fluid temperature on the fluid density since the material elastic modulus decreases as temperature increases.

The scheme for driving the tube 132 of the device of FIGS. 6 and 7 consists of a transformer of which the driving tube forms a short circuited, single turn secondary. Currents in the transformer primary generate much higher currents in the tube. These currents in the tube produce a magnetic field around the tube which interacts with the field from the permanent magnet 146 to produce forces which drive the tube in vibratory mode as a cantilever beam. When the primary is connected to appropriate electronic driving circuitry it forms an oscillator running at the natural resonant frequency of the tube. In such circuitry the transformer and shorted secondary tube in the permanent magnet appear to be a resonant circuit with 90° phase shift occurring at resonance. The advantage of this form of drive for the resonant U-shaped tube 132 include simple, low cost construction with no critical tolerances, alignments, or adjustments being required. It uses small numbers of simple parts. The resonant tube is as light as possible due to the absence of attached armatures or driving apparatus. This in turn yields a high change in frequency for a given change in fluid density.

In all of the embodiments, the means to introduce and/or eject the sample fluid may comprise a pressure pump or a vacuum pump or a syringe with or without valving. The pump could run continuously with fluid flow being controlled by a fluid valve or by a vacuum pump valve or the pump could be turned on and off. The used sample could be returned to the original sample container or another waste receptacle or could be introduced into a vessel for further tests, such as centrifugation.

Furthermore, the means for inducing currents in the tube is not limited to making the tube a single turn, short circuited secondary of a transformer. The tube could be connected directly to a suitable current source if the support housing is electrically rendered non-conductive by suitable insulation means.

Additionally, the instrument may be a fully self-contained, portable, single housing unit containing, for example, the tube, tip, housing, vibrating means, electronics, readout, battery, syringe pump, and waste receptacle. When not in use it would be placed on a stand which would keep the batteries charged in a conventional manner.

Thus the several aforenoted objects and advantages are most effectively attained. Although several somewhat preferred embodiments have been disclosed and described in detail herein, it should be understood that this invention is in no sense limited thereby and its scope is to be determined by that of the appended claims.

I claim:

1. Apparatus for measuring fluid specific gravity comprising; a housing, a hollow tube mounted in the housing and open at both ends, means on the housing for communication with a source of fluid to be introduced into one end of the hollow tube, means on the housing for connection of pressure differential means to the other end of the hollow tube for causing fluid to flow from the fluid source into the hollow tube, vibration means for vibrating the tube containing the fluid at its natural resonant frequency by the interaction of the magnetic field generated by alternating current passed through the tube and a steady magnetic field generated by a permanent magnet, temperature sensing means for automatically compensating for fluid temperature differences affecting sample density and vibrating tube elastic modulus and response means to measure the vibration frequency of the tube and sample therein and compare the measurement with a predetermined reference frequency correlated to the substance on whose density the specific gravity is based to determine the specific gravity of the fluid.

2. The invention in accordance with claim 1 wherein the pressure differential means is a vacuum source.

3. The invention in accordance with claim 1 wherein the fluid being measured is urine.

4. The invention in accordance with claim 1 wherein the response means is activated while fluid is passing through the tube.

5. The invention in accordance with claim 4 wherein the housing is a hollow elongated tubular member with end walls, each end wall having a passageway therethrough which extends through a projection extending outwardly from each end wall, a disposable sample tip mounted on one projection on one end wall and a tube connected to the projection extending from the other end wall, the hollow tube mounted in the housing end walls with the passageway therethrough in communication with the passageway through the end walls so that fluid can pass from a removable disposable tip mounted on one end of the housing through the hollow tube and out through the tube connected to the opening in the opposite end wall for collection, the temperature sensing means being a thermistor mounted in the housing so as to sense temperature change in the housing and accordingly in the fluid passing through the tube within the housing.

6. The invention in accordance with claim 5 wherein a valve means is positioned in the fluid flow path from the disposable tip at one end and the tube extending from the opposite end of the housing to open and close the flow path through the apparatus as desired, a waster reservoir connected to the tubing extending from the housing for collection of the fluid therein, a vacuum pump connected to the waste reservoir which when activated provides a vacuum condition within the reservoir so that when the valve in the fluid path is opened fluid will be drawn through the disposable tip, through the hollow tube in the housing and through the tube extending from the housing into the waste reservoir whereupon simultaneous activation of the driving electromagnet and thermistor will result in operation of the response means to measure the specific gravity on the fluid.

7. The invention in accordance with claim 1 wherein the vibration means and response means include electronic circuitry to cooperate in operating the apparatus and obtaining the determination of the specific gravity of the fluid passing therethrough.

8. The invention in accordance with claim 7 wherein electronic means includes a digital readout portion to provide a visual display of the specific gravity after it has been determined by the response means.

9. The invention in accordance with claim 1 wherein the hollow tube is a U-shaped tube open at both ends so that the fluid can enter one end of the tube pass therethrough and exit the other end thereof, the U-shaped tube being mounted adjacent to its ends so that the closed end is free to act as a cantilever and facilitate vibration of the U-shaped tube.

10. The invention in accordance with claim 1 wherein the housing is in the form of a hand held instrument.

11. A method of measuring fluid specific gravity comprising; providing a hollow tube mounted in a housing and open at both ends, connecting one end of the hollow tube with a pressure differential means, positioning the other end of the hollow tube in communication with a source of fluid, introducing fluid into the hollow tube, vibrating the tube at its natural resonant frequency by the interaction of the magnetic field generated by alternating current passed through the tube and a steady magnetic field generated by a permanent magnet, measuring the vibration frequency of the tube with the fluid contained therein and comparing the measurement with a predetermined reference frequency related to the substance on whose density the specific gravity is based to determine the specific gravity of the fluid.

12. The invention in accordance with claim 11 wherein the hollow tube is connected to a vacuum source and the fluid is sectioned into the tube.

13. The invention in accordance with claim 11 wherein the resultant specific gravity measurement of the fluid is visually displayed.

14. The invention in accordance with claim 11 where the fluid in the tube is urine.

15. The invention in accordance with claim 11 wherein the temperature of the fluid passing through the tube is monitored and is introduced into the computation of measuring of specific gravity to increase the accuracy thereof and the vibration frequency is measured as the fluid passes through the tube.

16. The invention in accordance with claim 15 wherein the temperature sensitive means is a termistor located in proximal relationship to the fluid sample in the tube.

17. The invention in accordance with claim 15 wherein the pressure differential means includes a vacuum source and the vacuum source is provided by a vacuum pump communicating through a waste reservoir through a connector tube to the hollow tube for passage of fluids through the hollow tube and into the waste reservoir subject to pressure differential caused by the vacuum pump.

18. The invention in accordance with claim 15 wherein the hollow tube is mounted in a surrounding housing open at both ends to permit communication to both ends of the hollow tube, a disposable tip mounted on one end of the housing for introduction to the fluid source to permit passage of fluid therethrough and through the housing into the hollow tube, the disposable tip being removable from the housing for disposal after use.

19. The invention in accordance with claim 11 wherein the hollow tube is U-shaped in configuration and is supported in the housing adjacent its closed ends so that the closed end of the U-shaped tube vibrates as a cantilever when subject to forces from an adjacent magnet.

* * * * *

UNITED STATES PATENT OFFICE
CERTIFICATE OF CORRECTION

PATENT NO. : 4,074,562
DATED : February 21, 1978
INVENTOR(S) : Howard L. North, Jr.

It is certified that error appears in the above-identified patent and that said Letters Patent are hereby corrected as shown below:

Col. 1, line 65, the word "object" should read --objective--.

Col. 4, line 43, the word "water" should read --waste--.

Col. 4, line 54, the word "time" should read --timed--.

Col. 8, line 46, the word "related" should read --correlated--.

Col. 8, line 51, the word "sectioned" should read --suctioned--.

Col. 8, line 64, the word "termistor" should read --thermistor--.

Signed and Sealed this

Twenty-second Day of August 1978

[SEAL]

Attest:

RUTH C. MASON
Attesting Officer

DONALD W. BANNER
Commissioner of Patents and Trademarks